US012678555B2

(12) United States Patent
Bolognia et al.

(10) Patent No.: US 12,678,555 B2
(45) Date of Patent: Jul. 14, 2026

(54) FLUID DELIVERY SYSTEM

(71) Applicant: Analog Devices, Inc., Norwood, MA (US)

(72) Inventors: David Frank Bolognia, Charlestown, MA (US); J Brian Harrington, Upton, MA (US); Vikram Venkatadri, Ayer, MA (US)

(73) Assignee: Analog Devices, Inc., Norwood, MA (US)

( * ) Notice: Subject to any disclaimer, the term of this patent is extended or adjusted under 35 U.S.C. 154(b) by 407 days.

(21) Appl. No.: 17/005,222

(22) Filed: Aug. 27, 2020

(65) Prior Publication Data

US 2022/0062535 A1     Mar. 3, 2022

(51) Int. Cl.
| | |
|---|---|
| *A61M 5/142* | (2006.01) |
| *A61M 5/168* | (2006.01) |
| *A61M 39/22* | (2006.01) |

(52) U.S. Cl.
CPC .... *A61M 5/14244* (2013.01); *A61M 5/16886* (2013.01); *A61M 39/227* (2013.01); *A61M 2205/3334* (2013.01); *A61M 2205/36* (2013.01)

(58) Field of Classification Search
CPC ...... A61M 5/14244; A61M 2205/3334; A61M 2205/36; A61M 5/14593; A61M 5/16813; A61M 5/16886; A61M 2039/2433; A61M 39/22; A61M 39/227; A61M 2205/127; A61M 2205/128; A61M 5/16881; A61M 5/16804; A61M 5/16809; A61M 39/228; A61M 5/152; F04B 13/00; F04B 17/00;
(Continued)

(56) References Cited

U.S. PATENT DOCUMENTS

| | | | |
|---|---|---|---|
| 2,729,976 | A | 1/1956 | Laub |
| 2,911,827 | A | 11/1959 | Hanks |
| 3,845,814 | A | 11/1974 | Kun |

(Continued)

FOREIGN PATENT DOCUMENTS

| | | |
|---|---|---|
| DE | 10 2014 202 853 A1 | 8/2015 |
| DE | 10 2014 112 261 A1 | 3/2016 |

(Continued)

OTHER PUBLICATIONS

International Search Report and Written Opinion in International Application No. PCT/US2021/047551, mailed on Nov. 25, 2021.
(Continued)

*Primary Examiner* — Kami A Bosworth
*Assistant Examiner* — Avery Smale
(74) *Attorney, Agent, or Firm* — Knobbe, Martens, Olson & Bear, LLP

(57) ABSTRACT

A flow control system is disclosed. The flow control system can include a flow meter positioned at a first location of a flow path of a fluid substance, and a valve positioned at a second location of the flow path of the fluid substance. The flow meter can include a molded non-conductive housing, a heating element that is at least partially embedded in the housing, and a sensing element that is at least partially embedded in the housing. The valve can open the flow path to allow the fluid substance to flow in the flow path. The valve can include an actuator that includes deformable chamber and a gate in the flow path of the fluid substance.

22 Claims, 10 Drawing Sheets

(58) Field of Classification Search

CPC . F04B 53/10; F16K 3/00; F16K 31/12; F16K 7/17

See application file for complete search history.

(56) References Cited

U.S. PATENT DOCUMENTS

| | | | |
|---|---|---|---|
| 3,894,538 | A | 7/1975 | Richter |
| 4,155,362 | A | 5/1979 | Jess |
| 4,335,835 | A | 6/1982 | Beigler et al. |
| 4,587,843 | A | 5/1986 | Tokura et al. |
| 4,677,850 | A | 7/1987 | Miura et al. |
| 4,688,424 | A | 8/1987 | Handtmann et al. |
| 4,829,818 | A | 5/1989 | Bohrer |
| 4,912,974 | A | 4/1990 | Inada et al. |
| 5,073,094 | A | 12/1991 | Dorman et al. |
| 5,081,866 | A | 1/1992 | Ochiai et al. |
| 5,222,395 | A | 6/1993 | Matubara et al. |
| 5,269,443 | A | 12/1993 | Lancaster |
| 5,527,288 | A | 6/1996 | Gross et al. |
| 5,792,952 | A | 8/1998 | Ritchart |
| 5,831,159 | A | 11/1998 | Renger |
| 6,537,437 | B1 | 3/2003 | Galambos et al. |
| 6,591,674 | B2 | 7/2003 | Gehman et al. |
| 6,607,495 | B1 | 8/2003 | Shalak et al. |
| 6,699,234 | B2 | 3/2004 | Yeh |
| 6,889,559 | B2 | 5/2005 | Gimson |
| 7,096,729 | B2 | 8/2006 | Repko et al. |
| 7,231,839 | B2 | 6/2007 | Huber et al. |
| 7,985,057 | B2 | 7/2011 | Haar |
| 8,088,333 | B2 | 1/2012 | Ahmad |
| 8,226,597 | B2 | 7/2012 | Jacobson et al. |
| 8,756,990 | B2 | 6/2014 | Speldrich |
| 9,132,231 | B2 | 9/2015 | Gross et al. |
| 9,492,614 | B2 | 11/2016 | Kamen et al. |
| 9,599,496 | B2 | 3/2017 | Asano et al. |
| 9,616,171 | B2 | 4/2017 | Qin et al. |
| 9,661,408 | B2 | 5/2017 | Kierse et al. |
| 10,191,023 | B2 | 1/2019 | Bather et al. |
| 11,604,084 | B2 | 3/2023 | Bolognia et al. |
| 11,712,516 | B2 | 8/2023 | Bolognia et al. |
| 11,796,367 | B2 | 10/2023 | Venkatadri et al. |
| 2005/0045480 | A1* | 3/2005 | Krumme ............ F16K 31/1266 204/600 |
| 2006/0079862 | A1 | 4/2006 | Genosar |
| 2008/0097319 | A1 | 4/2008 | Shih et al. |
| 2011/0060280 | A1* | 3/2011 | Caffey ................. A61M 37/00 604/151 |
| 2011/0177411 | A1 | 7/2011 | Wu et al. |
| 2011/0275996 | A1 | 11/2011 | Gyory et al. |
| 2013/0237955 | A1* | 9/2013 | Neta ................. A61M 5/16831 604/113 |
| 2014/0135699 | A1 | 5/2014 | Gyory |
| 2016/0105737 | A1 | 4/2016 | Kierse et al. |
| 2017/0021145 | A1* | 1/2017 | Saul ................... F16K 99/0057 |
| 2017/0115149 | A1 | 4/2017 | Silpachai et al. |
| 2017/0232189 | A1 | 8/2017 | Qin et al. |
| 2018/0058894 | A1 | 3/2018 | Pearson et al. |
| 2018/0266984 | A1 | 9/2018 | Pratt et al. |
| 2019/0126018 | A1 | 5/2019 | Browd et al. |
| 2019/0135614 | A1 | 5/2019 | Kierse et al. |
| 2019/0184095 | A1 | 6/2019 | Kim et al. |
| 2019/0255254 | A1 | 8/2019 | Wilmont et al. |
| 2020/0158791 | A1 | 5/2020 | Marauska et al. |
| 2020/0405981 | A1* | 12/2020 | Chen ................... A61M 11/042 |
| 2021/0180586 | A1 | 6/2021 | Bozic |
| 2021/0196884 | A1 | 7/2021 | Kim et al. |
| 2021/0322681 | A1 | 10/2021 | Bolognia et al. |
| 2021/0322709 | A1* | 10/2021 | Kopalli ............. A61M 16/0051 |
| 2022/0008637 | A1* | 1/2022 | Kumar ................... A61B 5/026 |
| 2022/0333958 | A1 | 10/2022 | Bolognia et al. |
| 2022/0357192 | A1 | 11/2022 | Venkatadri et al. |

FOREIGN PATENT DOCUMENTS

| | | | |
|---|---|---|---|
| EP | 3616737 | A2 | 3/2020 |
| EP | 4135792 | A | 2/2023 |
| EP | 4204068 | A1 | 7/2023 |
| GB | 1452104 | | 10/1976 |
| WO | WO 95/13839 | | 5/1995 |
| WO | WO 2012/159026 | A1 | 11/2012 |
| WO | WO 2020/040519 | A1 | 2/2020 |

OTHER PUBLICATIONS

Seo et al., "Rapid detection of COVID-19 causative virus (SARS-CoV-2) in human nasopharyngeal swab specimens using field-effect-transistor-based biosensor," ACS Nano 2020, American Chemical Society, vol. 14, pp. 5135-5142.

International Search Report and Written Opinion in International Application No. PCT/US2021/027412, mailed on Aug. 13, 2021.

Extended European Search Report in Application No. EP 21788171.3, mailed on Mar. 18, 2024 in 10 pages.

Office Action in European Application No. 21772916.9 dated Feb. 19, 2025 in 6 pages.

* cited by examiner

FLUID DELIVERY SYSTEM

CROSS-REFERENCE TO RELATED APPLICATIONS

This application is related to U.S. patent application Ser. No. 16/851,798, entitled "FLUID DELIVERY DEVICE," filed Apr. 17, 2020, and U.S. patent application Ser. No. 16/859,665, entitled "DEVICE WITH CHEMICAL REACTION CHAMBER," filed Apr. 27, 2020, the entire disclosures of which are incorporated herein by reference for all purposes.

BACKGROUND

Field

The field relates to flow control systems and, in particular, to fluid substance flow control systems.

Description of the Related Art

Substance delivery systems can deliver a substance, e.g., a fluid substance, from one location to another. An example of a substance delivery system is a drug delivery system. In a drug delivery system, a drug can be stored in one place and the drug can be delivered to a patient's body. It can be important to controllably deliver a desired amount of the fluid to the patient's body.

SUMMARY

In one aspect, a fluid delivery system is disclosed. the fluid delivery system can deliver a biocompatible fluid. The fluid delivery system includes a valve that is positioned at a first location of a flow path of a fluid substance. The valve includes an actuator that includes a deformable chamber and a gate in the flow path of the fluid substance. The gate is configured to open in response to deformation of the deformable chamber so as to allow the fluid substance to flow in the flow path.

In one embodiment, the actuator includes an electroosmotic (EO) pump. The EO pump can include a second deformable chamber, a porous electrode that is positioned between the deformable chamber and the second chamber, and a porous membrane that is positioned between the deformable chamber and the second chamber. The deformable chamber and the second deformable chamber can be in fluid communication.

In one embodiment, the fluid delivery system further includes a flow meter that is positioned at a second location of a flow path of a fluid substance. The flow meter can include a molded non-conductive housing, a heating element that is at least partially embedded in the housing, and a sensing element that is at least partially embedded in the housing. The fluid delivery system can further include a pump that is configured to drive the fluid substance along the fluid flow path through the valve and the flow meter.

In one embodiment, the fluid delivery system further includes a controller that is in electrical communication with the valve. The controller can be configured to control operation of the flow control system.

In one aspect, a fluid delivery system is disclosed. The fluid delivery system can deliver a biocompatible fluid. The fluid delivery system includes a flow meter that is positioned in a fluid flow path. The fluid delivery system also includes a valve that is positioned in the fluid flow path. The valve includes an actuator that has a deformable chamber. The deformable chamber is configured to open or close the fluid flow path to allow a fluid substance to flow in the flow path. The fluid delivery system further includes a pump that is configured to drive the fluid substance along the fluid flow path through the valve and the flow meter.

In one embodiment, the valve comprises an electroosmotic (EO) pump.

In one embodiment, the pump comprises an electroosmotic (EO) pump.

In one embodiment, the flow meter further includes a molded non-conductive housing, a heating element that is at least partially embedded in the housing, and a sensing element that is at least partially embedded in the housing.

In one embodiment, the fluid delivery system further includes a controller that is in electrical communication with the flow meter, the valve, and the pump. The controller can be configured to control operation of the substance delivery system.

In one aspect, a fluid delivery system is disclosed. The fluid delivery system can deliver a biocompatible fluid. The fluid delivery system includes a flow meter that is positioned at a first location of a flow path of a fluid substance. The flow meter includes a molded non-conductive housing, a heating element that is at least partially embedded in the housing and exposed to the flow path, and a sensing element that is at least partially embedded in the housing and exposed to the flow path. The heating element is configured to transfer thermal energy to the fluid substance in the flow path, and the sensing element is configured to transduce thermal energy from the flow path to an electrical signal.

In one embodiment, the heating element and the sensing element are arranged to contact the fluid substance during operation of the drug delivery system.

In one embodiment, the heating element comprises a conductive plastic.

In one embodiment, the heating element is disposed at least partially around a portion of the flow path.

In one embodiment, the sensing element includes a conductive plastic.

In one embodiment, the sensing element at least partially conforms with a portion of the flow path.

In one embodiment, the flow path includes a hole through the housing. The hole can have a diameter in a range from 0.5 mm to 1 mm.

In one embodiment, the heating element and the sensing element are spaced apart from each other along the flow path. The space between the heating element and the sensing element can be at least 1 mm.

In one embodiment, the fluid delivery system further includes a second heating element that is positioned between the heating element and the sensing element.

In one embodiment, a volume of the flow path in the flow meter is between 0.1 $mm^3$ to 16 $mm^3$.

In one embodiment, the fluid delivery system further includes a valve that is positioned at a second location of the flow path of the fluid substance. The valve can be configured to control the flow of the fluid substance along the flow path. The valve can include an actuator. The actuator can include a deformable chamber. The valve can include a gate that is positioned in the flow path. The gate can be configured to open in response to deformation of the deformable chamber thereby allowing the fluid substance to flow in the flow path. The actuator can include an electroosmotic (EO) pump. The fluid delivery system can further include a pump that is configured to drive the fluid substance along the fluid flow path through the valve and the flow meter.

In one embodiment, the fluid delivery system further includes a controller that is in electrical communication with the flow meter. The controller can be configured to control operation of the flow control system. The controller can be configured to transmit current to the heating element, to receive a signal from the sensing element, and to determine at least one of a temperature and a flow rate based at least in part on the signal.

Details of one or more implementations of the subject matter described in this specification are set forth in the accompanying drawings and the description below. Other features, aspects, and advantages will become apparent from the description, the drawings, and the claims. Note that the relative dimensions of the following figures may not be drawn to scale.

BRIEF DESCRIPTION OF THE DRAWINGS

Embodiments of this disclosure will now be described, by way of non-limiting example, with reference to the accompanying drawings.

DETAILED DESCRIPTION

Figure 1:
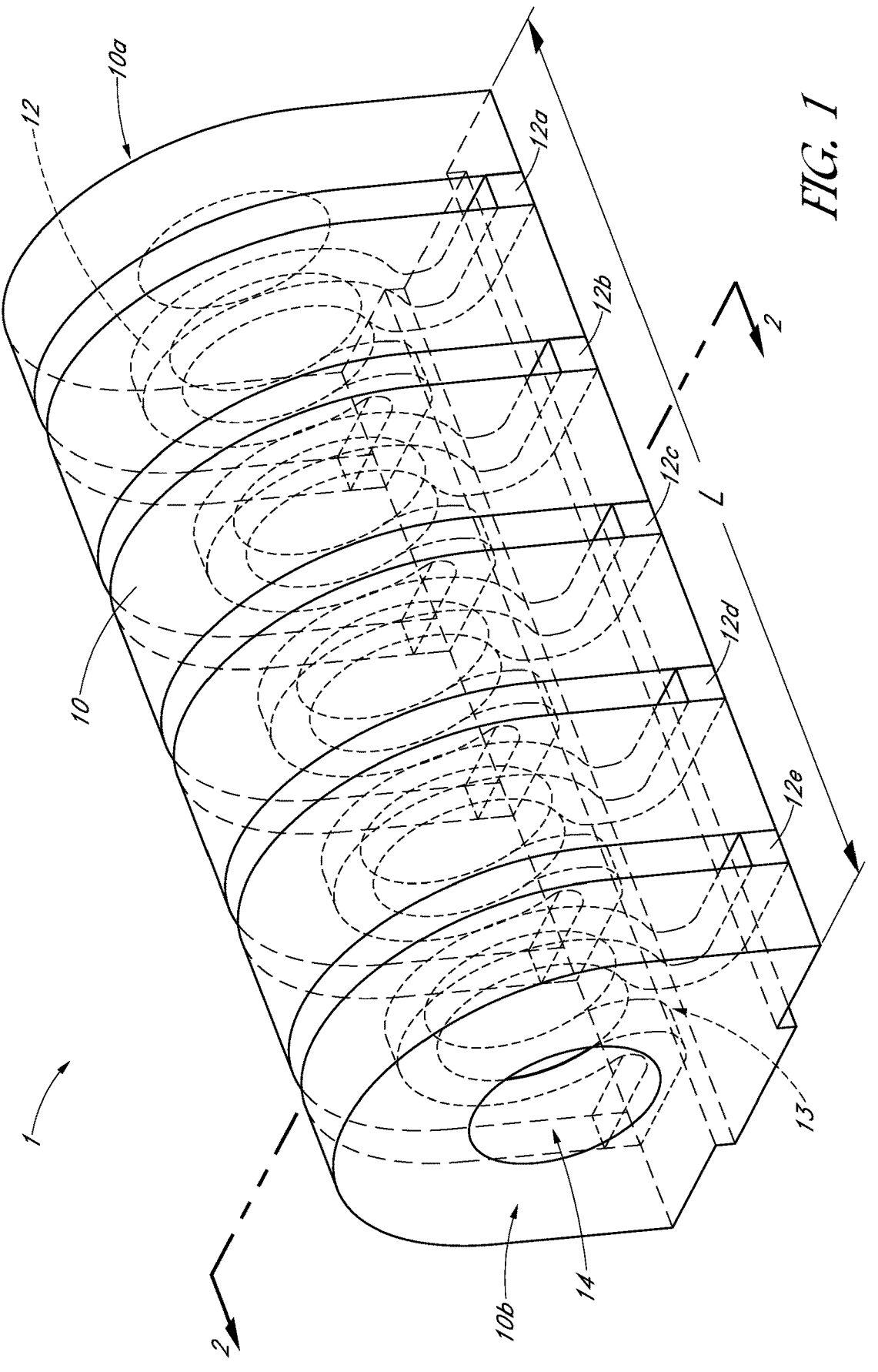
FIG. 1 is a schematic perspective view of a flow meter according to one embodiment.

Substance delivery systems, for example, a drug delivery system, can be used to deliver a fluid substance (e.g., a drug) disposed in a reservoir to a target location (e.g., inside a patient's vasculature, into analysis equipment, or to any other suitable target location). The drug can include, for example, insulin for treating diabetes, an anti-nausea drug for chemotherapy, etc. The drug delivery system can include a flow control system and a drug delivery device.

The flow control system can include a flow meter. The flow meter can monitor/measure a flow rate and/or a flow amount (e.g., volume) of the substance. The flow meter can be associated with the drug delivery device to manage the flow rate and a volume of the substance to deliver to the target location. As one example, it can be important to accurately and repeatedly monitor an amount of insulin delivered to a diabetic patient and to control the timing of the delivery. However, a conventional flow meter can be relatively large in size, and it can be difficult to measure or monitor the flow rate and/or the flow amount of the substance with a relatively fine accuracy. Also, the large size of conventional flow meters can be undesirable for certain applications, such as for use in a wearable device.

The flow control system can include a valve. The valve can function as, for example, a shutoff valve and/or a check valve. When the valve functions as a shutoff valve, the valve can alternately open to permit flow of the fluid substance and close to shut of the flow of the fluid substance. When the valve functions as a check valve, it can prevent or mitigate a backflow of the fluid substance. The flow meter can be associated with the valve to manage the operation of the valve. For example, the flow control system can include a controller in electrical communication with the valve and the flow meter. The controller can send instructions to the valve to open and/or close the valve based on signals received from the flow meter. The valve can include a gate that can open and/or close to control the flow of the substance. The valve can include a mechanical actuator that can cause the gate to open and/or close. Conventional mechanical actuators can be relatively large in size and can require relatively high power to operate. Therefore, such conventional actuators can be undesirable for certain applications, such as for use in a wearable device. Beneficially, the embodiments disclosed herein provide accurate flow measurement and control in a small form factor that may be wearable and/or portable.

Various embodiments disclosed herein relate to a flow control system that includes a flow meter that can measure/monitor a flow rate and/or a flow amount of the substance with a relatively fine accuracy. In some embodiments, the flow meter can include a non-conductive housing and a conductive portion. The housing can comprise a molded non-conductive housing. The conductive portion can comprise a heater and a sensor. The heater and/or the sensor can be at least partially embedded in the housing. The conductive portion can comprise a conductive plastic. The flow meter can be manufactured using a two shot molding process in which the conductive portion and the housing are separately formed by a molding process. In some embodiments, the conductive portion of the flow meter can include two or more heaters. In some embodiments, the conductive portion of the flow meter can include two or more sensors.

Various embodiments disclosed herein relate to a flow control system that includes a valve that includes a pump that operates with a relatively low power, and a gate. For example, the pump can comprise an electroosmotic (EO) pump. The pump can include an expandable or deformable chamber configured to receive and contain a solution (e.g., an electrolyte) therein. The expandable or deformable chamber can include an elastic or expandable diaphragm that can expand in response to a pressure difference in the chamber caused by a movement or a volumetric expansion of the solution in the chamber. The solution can comprise any suitable solution. For example, the solution can comprise reverse osmosis (RO) water. The expansion of the diaphragm can actuate the gate to open/close. The gate can have a closed state in which the gate is completely closed. The gate can have an opened state. The opened state can comprise a fully opened state in which the gate is fully/completely opened. The opened state can comprise an intermediate state in which the gate is partially opened. The intermediate state can be a state in between the closed state and the fully opened state, which can enable a non-zero flow through the valve that is less than the flow rate in the opened state.

FIG. 1 is a schematic perspective view of a flow meter 1 according to one embodiment. The flow meter can comprise a housing 10, a conductive material 12, and a flow path 14 at least partially defined by the housing 10. In FIG. 1, the housing 10 is shown transparent to illustrate its internal structure. The flow meter 1 can comprise any suitable shape. For example, the housing 10 can be shaped such that the flow path 14 comprises a rounded (e.g., generally cylindrical) shape as illustrated herein. The housing 10 can comprise a housing body that is curved (e.g., generally cylindrical) with one or more planar support surfaces below the curved body. The conductive material 12 can comprise flow transducing elements 12a-12e. The elements 12a-12e can comprise flow transducing elements that can include a heating element and/or a sensing element. In some embodiments, one or more of the elements 12a-12e can comprise and function as a heater and the rest of the elements 12a-12e can comprise and function as a sensor. For example, elements 12a and 12b can comprise heating elements and elements 12c-12e can comprise sensing elements. As another example, elements 12b and 12c can comprise heating elements and elements 12a, 12d, and 12e can comprise sensing elements. Though five elements 12a-12e are illustrated in FIG. 1, the flow meter 1 can comprise any suitable number of elements. In some embodiments, the flow meter 1 can comprise at least one heating element and at least one sensing element. A more accurate measurement may be achieved with more number of the heating element and/or more number of the sensing element.

In some embodiments, the flow meter 1 can be configured to measure or monitor a flow rate and/or a flow amount of a fluid substance (e.g., a drug) that flows through the flow path 14. For example, the fluid substance (not shown) can flow through the flow path 14 from a first end 10a of the housing 10 to a second end 10b of the housing 10 opposite the first end 10a, and the flow of the fluid substance can be measured or monitored using a temperature difference of the fluid substance in the flow path 14. In such embodiments, the flow meter 1 can comprise additional components (not illustrated) and/or can be coupled to an external device (not illustrated) that can operate the flow meter and/or analyze data obtained through the sensing elements. In some embodiments, the additional components or the external device can comprise a controller 9 (see FIG. 7).

In some embodiments, the flow meter 1 can comprise a heating element positioned upstream of a sensing element in the flow path 14. The heating element positioned upstream of the sensing element can apply heat to the fluid substance in the flow path 14, and the sensing element positioned downstream of the heating element can sense a heat loss of the fluid substance in the flow path 14.

In some embodiments, the flow meter 1 can comprise a first heating element 12a, a second heating element 12b, a first sensing element 12c, a second sensing element 12d, and a third sensing element 12e. In such embodiments, the first and second heating elements 12a, 12b can apply heat to the fluid substance by pulsing current through the heating elements 12a, 12b. In some embodiments, the controller 9 can cause current to be transmitted (e.g., pulsed) to the heating elements 12a, 12b sequentially by the additional components or the external device can. In some embodiments, the heating element 12a, 12b can provide a temperature difference (ΔT) of, for example, about 10° C. to the fluid substance. The temperature difference (ΔT) can be the difference between a temperature of the fluid substance upstream of the heating element 12a, 12b and a temperature of the fluid substance downstream of the heating element 12a, 12b.

A first temperature of the fluid substance can be measured through the first sensing element 12c, a second temperature of the fluid substance can be measured through the second sensing element 12d, and a third temperature of the fluid substance can be measured through the third sensing element 12e. The controller 9 (or other external computing device) coupled to the flow meter 1 can use the differences in the measured temperatures to determine the flow rate of the fluid substance.

The housing 10 can comprise any suitable non-conductive material. In some embodiments, the housing 10 can comprise a non-conductive molding material. For example, the housing 10 can comprise a molding material, such as plastic or polymer (e.g., liquid crystal polymer (LCP) or acrylonitrile butadiene styrene (ABS)). In some applications, such as when the fluid substance comprises a drug, the housing 10 can comprise a bio-compatible housing. For example, the housing 10 can comprise a biocompatible material that does not interact with the drug or with the human body. In some embodiments, the biocompatible material can comprise a biocompatible polymer. In some other embodiments, the biocompatible material can comprise a biocompatible metal, or a metal with a biocompatible coating. In various embodiments, the housing 10 can be cleaned so that the flow meter 1 (and other system components) can be reused. In other embodiments, the housing 10 (and other components of the flow meter 1) can be disposable after a suitable number of uses.

The conductive material 12 can comprise any suitable conductive material. In some embodiments, the conductive material 12 can comprise a conductive nano-wire. In some embodiments, the conductive nano-wire can comprise a molded conductive material. In some embodiments, the conductive nano-wire can comprise conductive plastic. The conductive plastic can comprise conductors integrated with plastic, such as a molded metal lead frame, or a molded lead frame with conductive non-metal materials, such as conductive ABS, embedded in a non-conductive plastic mold. The conductive plastic lead frame can include a lead frame that comprises plastic (e.g., liquid crystal polymer (LCP) or acrylonitrile butadiene styrene (ABS)) and carbon fiber. The carbon fiber or other conductive filler material can be mixed, embedded, or otherwise integrated with the plastic. In some embodiments, the conductive material 12 can comprise two or more materials and different elements 12a-12e may comprise different materials.

The element 12a-12e can at least partially conform with a portion of the flow path 14. For example, the elements 12a-12e can have curved profiles extending around the flow path 14. In some embodiments, the elements 12a-12e can be exposed to the flow path 14. In some embodiments, the elements 12a-12e can be in contact with the fluid substance that flows through the flow path 14. In some embodiments, the element 12a-12e can comprise an incomplete ring shape or omega shape. For example, in the illustrated embodiment, the elements 12a-12e may only partially surround the flow path 14, such that there is a gap 13 between radially-outward extending foot portions (e.g., feet 17, 19 shown in FIG. 2) of the elements 12a-12e.

The flow meter 1 has a length L from the first end 10a to the second end 10b. The flow meter 1 can have any suitable length L. In some embodiments, the length L of the flow meter 1 can be in a range from, for example, 2 mm to 5 mm, in a range from, for example, 2 mm to 4 mm, in a range from, for example, 3 mm to 5 mm, and in a range from, for example, 3 mm to 4 mm.

The elements 12a-12e of the flow meter 1 illustrated in FIG. 1 can be equally spaced along the flow path 14 (or the length L) of the flow meter 1. However, in some embodiments, spaces between the elements 12a-12e can vary. In some embodiments, a gap or spacing between one of the elements 12a-12e and an adjacent element 12a-12e can be about 1 mm. In some embodiments, the gap can be in a range from, for example, 0.5 mm to 2 mm, in a range from, for example, 0.5 m to 1.5 mm, in a range from, for example, 0.5 m to 1 mm, in a range from, for example, 1 m to 2 mm, or in a range from, for example, 1 m to 1.5 mm. In some embodiments, each of the heating/sensing elements 12a-12e can have a resistance in a range from, for example, 100Ω to 1000Ω, in a range from, for example, 100Ω to 500Ω, in a range from, for example, 300Ω to 1000Ω, in a range from, for example, 500Ω to 1000Ω, in a range from, for example, 300Ω to 500Ω.

Figure 2:
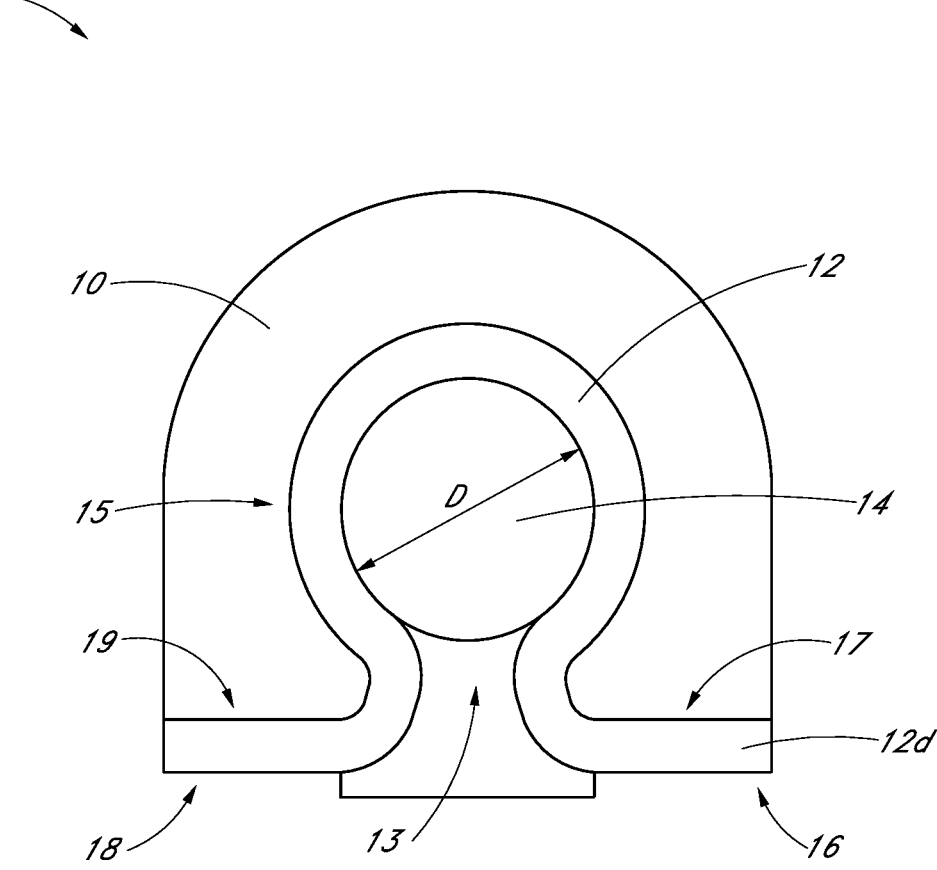
FIG. 2 is a schematic cross sectional side view of the flow meter of FIG. 1.

FIG. 2 is a schematic cross sectional side view taken along the element 12d of the flow meter 1 illustrated in FIG. 1. Cross sectional side views taken along other elements 12a, 12b, 12c, 12e can be the same as or generally similar to what is illustrated in FIG. 2. The flow meter 1 can have a round arched overall shape in the cross sectional side view as seen in FIG. 2, with a curved flow path 14 through at or near the center of the flow meter 1, and an omega shaped conductive material 12 at least partially around the flow path 14. For example, as explained above, the elements 12a-12e can have a rounded or curved portion 15 that extends around the flow path 14 and opposing feet 17, 19 that extend radially outward from the curved portion 15. In various embodiments, the curved portion 15 of the elements 12a-12e can extend around the flow path 14 by an angle greater than 180°, or greater than 270°. However, in other embodiments, the flow meter 1 can comprise any other suitable shapes and geometries.

As illustrated in FIG. 2, at least a portion of the elements 12a-12e can be exposed to the flow path 14 so as to contact the fluid substance that flows through the flow path 14, in some embodiments. It can be beneficial to have the elements 12a-12e contact the fluid substance in some embodiments as it can be operated with less power as compared to embodiments where the elements 12a-12e are not in contact with the fluid substance. However, in some other embodiments, the elements 12a-12e may be exposed to the flow path 14 without directly contacting the fluid substance. For example, a portion of the housing 10 can be disposed between the elements 12a-12e and the flow path 14. In some embodiments, the elements 12a-12e can be exposed to the flow path 14 by way of an intervening material or coating, such that the elements 12a-12e may not directly contact the fluid substance. Rather, the material or coating may physically intervene between the fluid substance and the elements 12a-12e, but the intervening material or coating may be sufficiently thermally conductive so as to effectively transfer heat between the elements 12a-12e and the fluid substance.

Each of the elements 12a-12e can comprise the feet 17, 19 that can include a first terminal 16 and a second terminal 18 respectively. In some embodiments, the first terminal 16 can comprise an input terminal and the second terminal 18 can comprise an output terminal. In some embodiment, the first terminal 16 can comprise an anode terminal and the second terminal 18 can comprise a cathode terminal. In some embodiments, the first terminal 16 and the second terminal 18 can be coupled to additional components (not illustrated) or an external component by way of conductive connectors, such as wires, ribbon interconnects and the like. In some embodiments, the first terminal 16 and the second terminal 18 can be configured to attach to the additional components or the external device by way of solder bumps. The additional components or the external device can comprise a controller 9 (see FIG. 7) configured to, for example, analyze data obtained through the sensing elements. In some embodiments, the first terminal 16 and the second terminal 18 can extend to define a dual in-line package (DIP) structure that can be mounted to a printed circuit board (PCB).

The flow path 14 of the flow meter 1 has a diameter D. The flow meter 1 can have any suitable diameter D. In some embodiments, the diameter D can be in a range from, for example, 0.5 mm to 1 mm, in a range from, for example, 0.5 mm to 0.8 mm, in a range from, for example, 0.5 mm to 0.7 mm, in a range from, for example, 0.7 mm to 1 mm, or in a range from, for example, 0.8 mm to 1 mm. For example, when the diameter D is 0.5 mm, a volume of the flow path between a heating element and a sensing element that is spaced apart by 1 mm can be about 0.196 mm$^3$ (or microliter). As such, a volume of the flow path between five elements that are spaced apart by 1 mm can be about 1 mm$^3$ (or microliter). For another example, when the diameter D is 0.5 mm, a volume of the flow path between a heating element and a sensing element that is spaced apart by 0.5 mm can be about 0.1 mm3 (or microliter). For another example, when the diameter D is 1 mm, a volume of the flow path between a heating element and a sensing element that is spaced apart by 5 mm can be about 4 mm$^3$ (or microliter). As such, a volume of the flow path 14 in the flow meter 1 can vary based at least in part on the diameter D and the length L of the flow meter 1. The volume of the flow path 14 in the flow meter 1 can be in a range of, for example, 0.1 mm$^3$ (or microliter) to 16 mm$^3$ (or microliter), in a range of, for example, 0.5 mm$^3$ (or microliter) to 16 mm$^3$ (or microliter), in a range of, for example, 3 mm$^3$ (or microliter) to 16 mm$^3$ (or microliter), in a range of, for example, 7 mm$^3$ (or microliter) to 16 mm$^3$ (or microliter), in a range of, for example, 0.1 mm$^3$ (or microliter) to 10 mm$^3$ (or microliter), in a range of, for example, 0.5 mm$^3$ (or microliter) to 5 mm$^3$ (or microliter), or in a range of, for example, 0.5 mm$^3$ (or microliter) to 3 mm$^3$ (or microliter).

In some applications, it can be preferred to have an accuracy of the flow rate measurement provided by the flow meter 1 to be about 1 μL/m or less. In some embodiments, the accuracy of the flow rate measurement provided by the flow meter 1 can depend at least in part on a volume of the flow path 14 within the flow meter 1. Accordingly, it can be important to design the size of the flow path 14 to be sufficiently small so as to provide an accuracy of the flow rate measurement that is desired for its application. In some embodiments, the flow meter 1 can be designed such that an accuracy of the flow rate measurement provided by the flow meter 1 is in a range of, for example, 0.5 μL/m to 1.5 μL/m, in a range of, for example, 0.5 μL/m to 1.2 μL/m, in a range of, for example, 0.7 μL/m to 1.5 μL/m, or in a range of, for example, 0.7 μL/m to 1.2 μL/m.

The flow meter 1 can be manufactured in various manufacturing processes. A method of manufacturing a flow meter 1 according to one embodiment can include forming a housing 10. The forming the housing 10 can comprise molding a non-conductive material. The molding the non-conductive material can comprise an injection molding process. The method can also include forming a conductive material 12. The forming the conductive material 12 can comprise forming an element 12a-12e. The forming the conductive material 12 can include molding the conductive material. The molding the conducive material can comprise an injection molding process. In some embodiments, the housing 10 and the conductive material 12 can be formed using a two shot molding process. In some embodiments, the housing 10 can be formed prior to forming the conductive material 12. The method can also include a singulation process in which a plurality of flow meters are singulated.

Figures 3A, 3B:
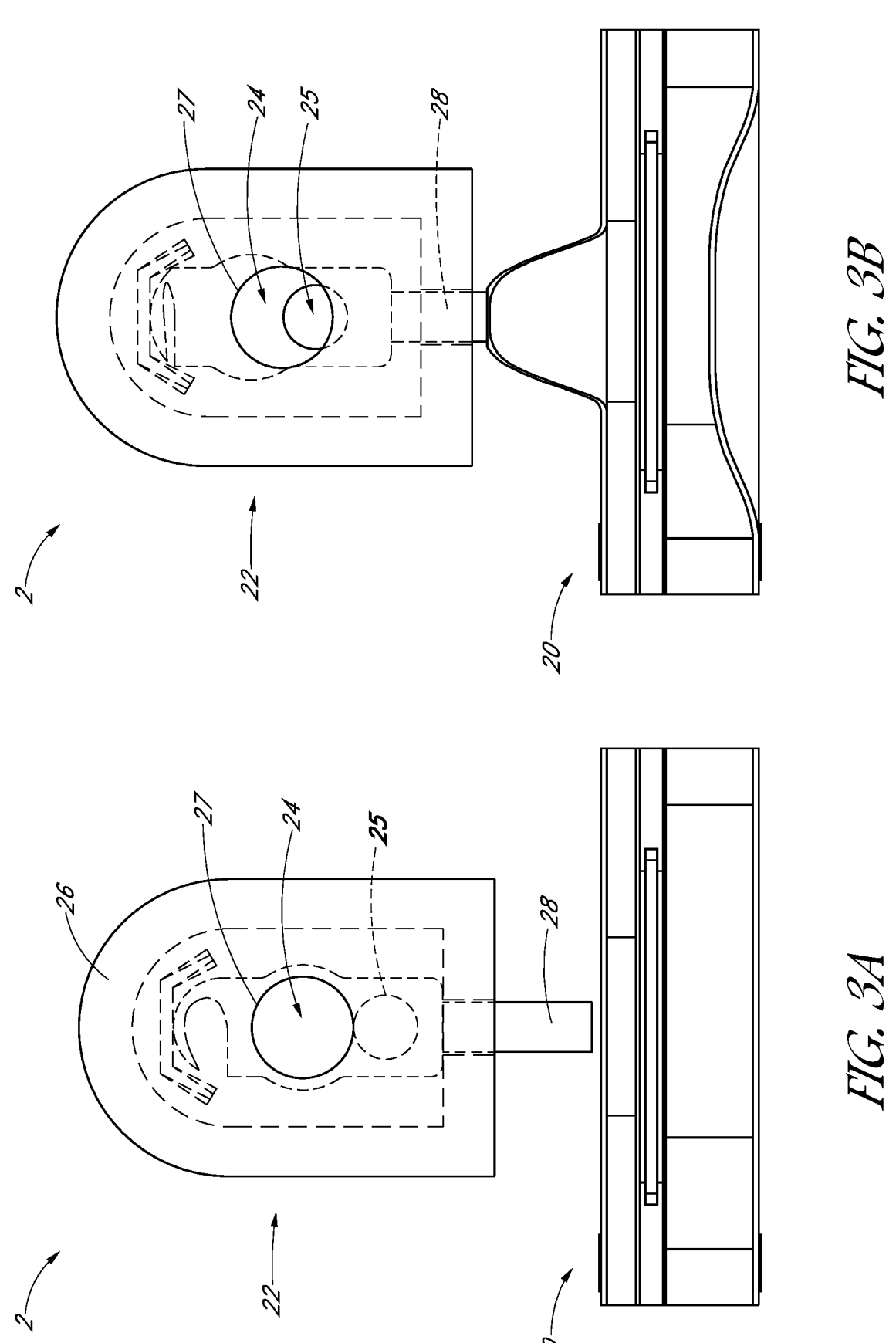
FIG. 3A is a schematic side view of a valve in a first state (e.g., a closed state) according to one embodiment.
FIG. 3B is a schematic side view of the valve illustrated in FIG. 3A in a second state (e.g., an opened state).

FIG. 3A is a schematic side view of a valve 2 in a first state (e.g., a closed state) according to one embodiment. FIG. 3B is a schematic side view of the valve 2 illustrated in FIG. 3A in a second state (e.g., an opened state). The valve 2 can comprise an actuator 20 and a gate structure 22 that includes a gate 24 and a gate housing 26. In FIGS. 3A and 3B, the gate housing 26 is shown transparent to illustrate internal components of the gate structure 22. The housing 26 can have a hole 27.

The actuator 20 can actuate (e.g., open/close) the gate 24 of the gate structure 22. A portion of the actuator 20 can directly or indirectly actuate the gate 24. For example, the portion of the actuator 20 can directly apply force to a movable element 28 of gate structure 22 so as to actuate the gate 24. The actuator 20 will be described more with respect to FIGS. 4A-5C.

In FIGS. 3A and 3B, the gate 24 is fully or completely closed in the first state and the gate 24 is fully or completely opened in the second state. However, the valve 2 can comprise an intermediate state in which the gate is partially opened or closed. The intermediate state can be any state in between the fully closed state and the fully opened state. In the intermediate state, fluid can flow through the valve 2 at a non-zero flow rate less than the flow rate through the valve 2 in the fully opened state. Accordingly, an opened state can comprise any state in which the gate 24 is not fully closed.

In some embodiments, the gate 24 can be in a closed state when no external force is applied to the movable element 28, for example, when the actuator 20 is inactivated. The gate structure 22 can comprise a mechanical element, such as a spring (not shown), that keeps the gate 24 closed when no external force is applied to the movable element 28. In such embodiments, the gate 24 can open when the actuator 20 applies force to the movable element 28 that is greater than the force applied to the movable element 28 by the spring. In such embodiments, the actuator 20 can apply a vertically upward force to cause the movable element 28 to translate along a direction transverse to a lateral dimension of the actuator 20. Vertical translation of the movable element 28 can move the gate 24 upward to expose an opening 25 through which the fluid can flow in the opened state(s). The opening 25 can be exposed when at least a portion of the opening 25 and the hole 27 align with each other. When a desired amount of the fluid substance has passed through the opening 25, the actuator 20 can be inactivated, and the spring or other biased mechanical structure can force the movable element 28 downward to cause the gate 24 to occlude the hole 27 and limit flow therethrough.

Figure 4A:
FIG. 4A is a schematic cross sectional side view of the actuator illustrated in FIGS. 3A and 3B in the first state.
Figure 4B:
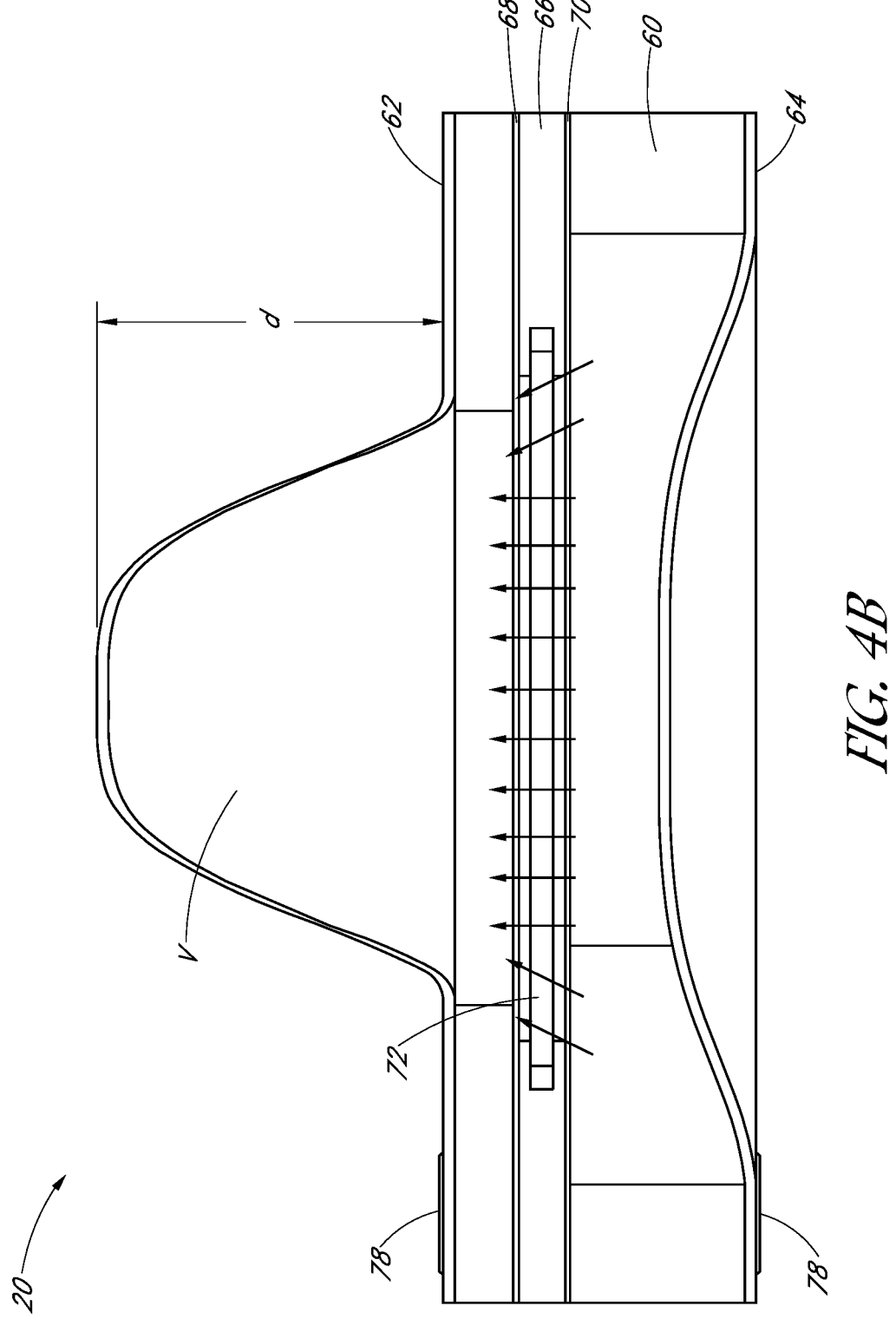
FIG. 4B is a schematic cross sectional side view of the actuator illustrated in FIGS. 3A-4A in the second state.
Figure 5A:
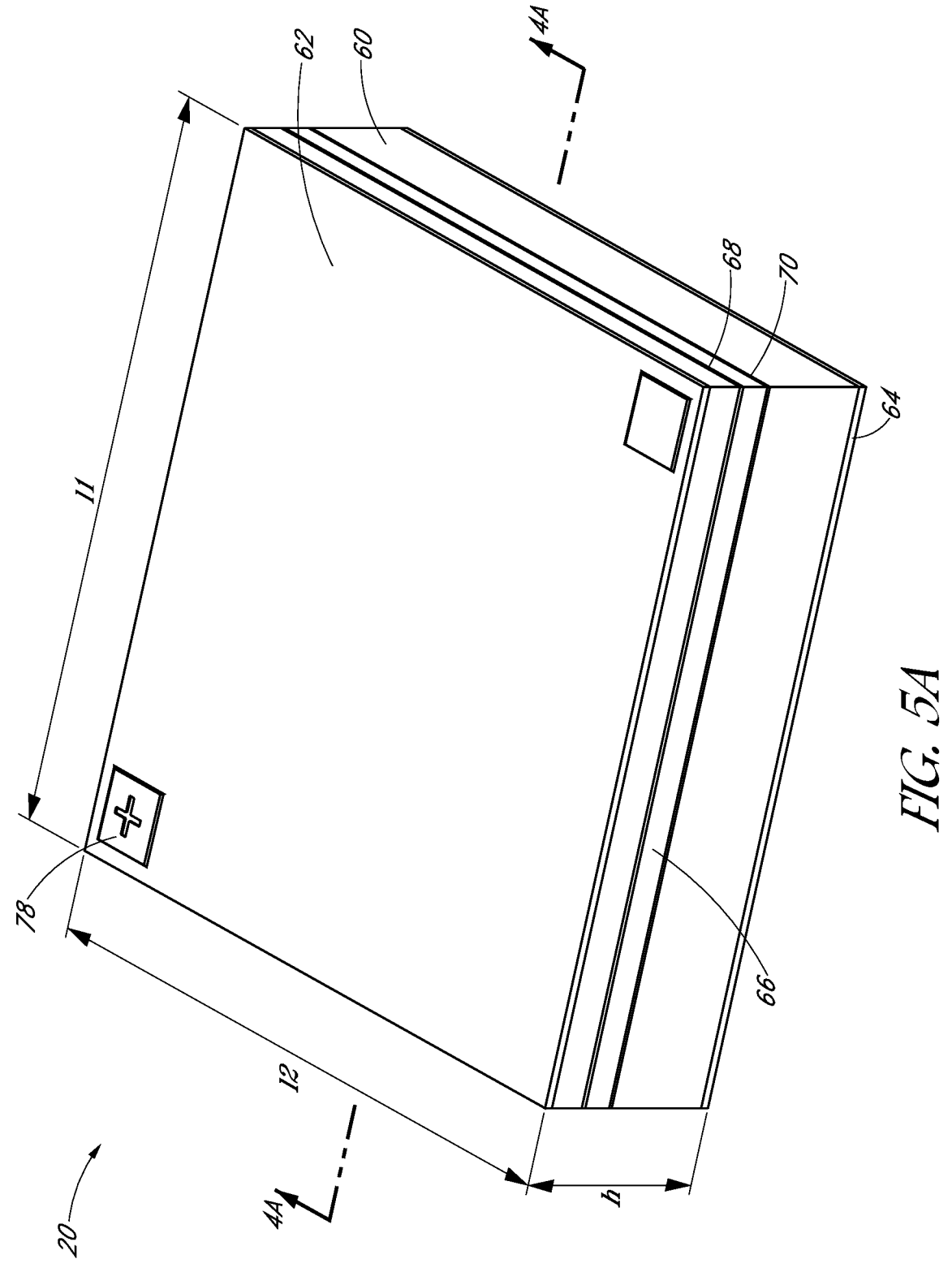
FIG. 5A is a schematic top perspective view of the actuator of FIG. 4A.
Figure 5B:
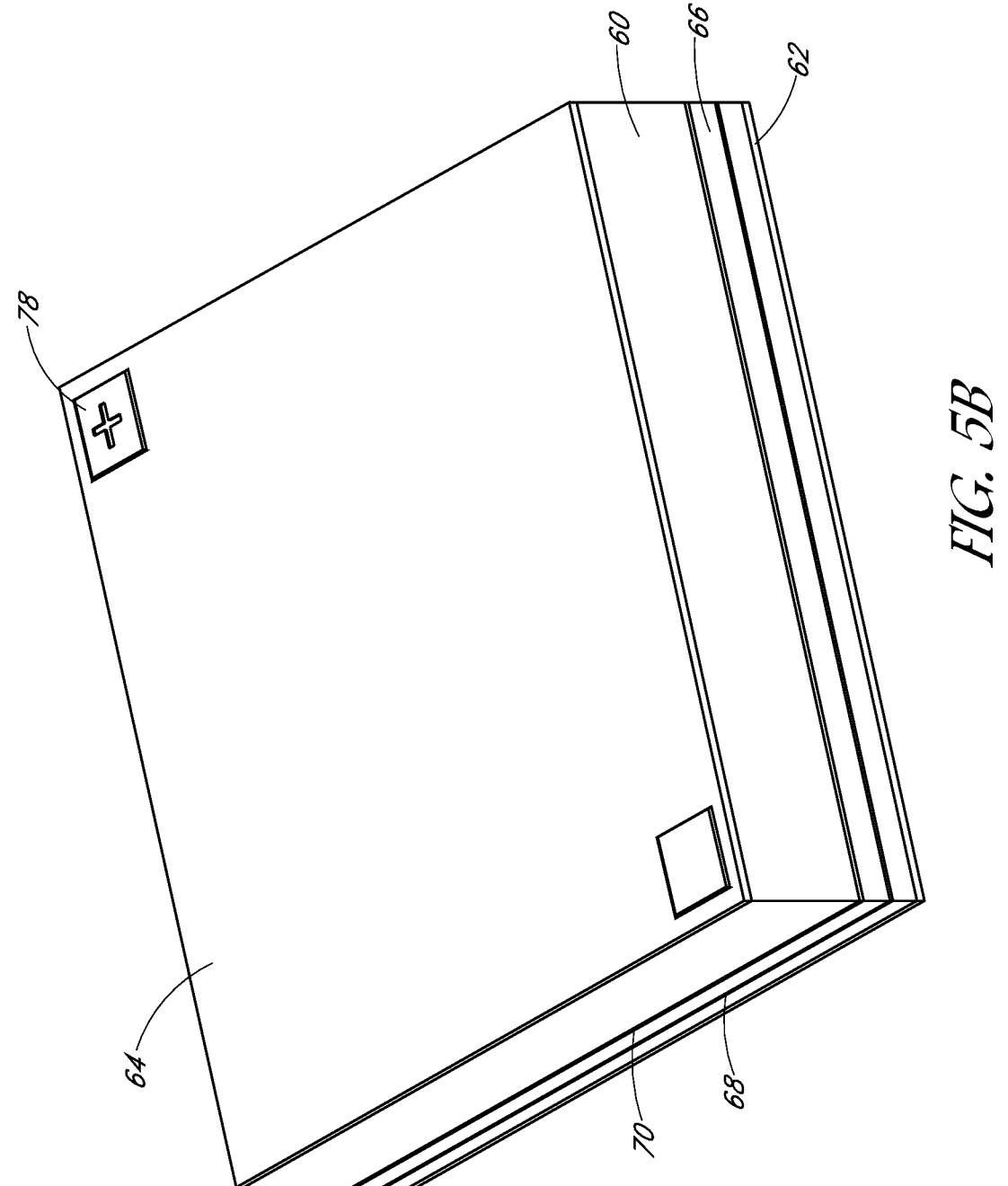
FIG. 5B is a schematic bottom perspective view of the actuator of FIG. 4B.
Figure 5C:
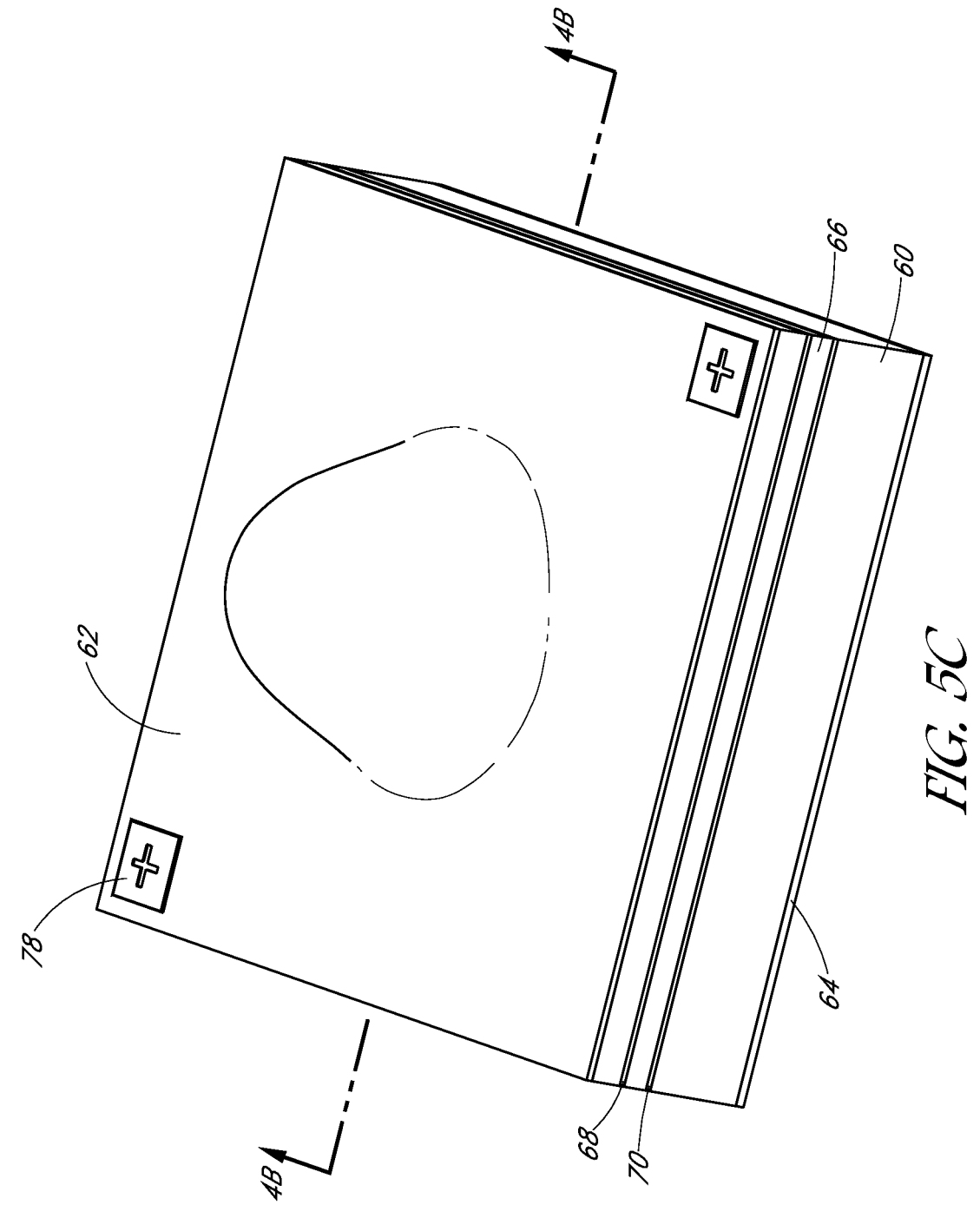
FIG. 5C is a schematic top perspective view of the actuator of FIG. 4B.

FIG. 4A is a schematic cross sectional side view of the actuator 20 illustrated in FIGS. 3A and 3B in a first state. FIG. 4B is a schematic cross sectional side view of the actuator 20 illustrated in FIGS. 3A-4A in a second state. FIG. 5A is a schematic top perspective view of the actuator 20 of FIG. 4A. FIG. 5B is a schematic bottom perspective view of the actuator 20 of FIG. 4B in the second state. FIG. 5C is a schematic top perspective view of the actuator 20 of FIG. 4B in the second state.

The actuator 20 illustrated in FIGS. 4A-5C can comprise an electroosmotic (EO) pump. The actuator 20 can comprise a housing 60, a first elastic diaphragm 62 that is attached to a first side (an upper side) of the housing 60, a second elastic diaphragm 64 that is attached to a second side (lower side)

of the housing 60, a spacer 66 that is positioned between the between the first side and the second side of the housing 60, a first electrode 68 that is positioned between the spacer 66 and the first elastic diaphragm 62, a second electrode 70 that is positioned between the spacer 66 and the second elastic diaphragm 64, and a porous membrane 72 positioned between the first electrode 68 and the second electrode 70. The actuator 20 can include a first chamber 74 defined at least partially by the housing 60 and the first elastic diaphragm 62, and a second chamber 76 defined at least partially by the housing 60 and the second elastic diaphragm 64. The first chamber 74 and the second chamber 76 are configured to receive a solution (e.g. reverse osmosis (RO) water). At least portions of the spacer 66, first electrode 68, and the second electrode 70 can be positioned between the first chamber 74 and the second chamber 76. In some embodiments, the portions of the spacer 66, first electrode 68, and the second electrode 70 positioned between the first chamber 74 and the second chamber 76 can provide fluid communication between the first chamber 74 and the second chamber 76. The actuator 20 can comprise contact pads 78 that can be electrically coupled to the first electrode 68 and the second electrode 70. In some embodiments, the contact pads 78 can be formed on or in a portion of the first elastic diaphragm 62 and or the second elastic diaphragm 64.

The first elastic diaphragm 62 and the second elastic diaphragm 64 can be sufficiently elastic so as to expand in response to an electroosmotic flow of a solution between the chambers 74, 76. In some embodiments, the expansions of the first elastic diaphragm 62 and the second elastic diaphragm 64 can maintain a pressure within the actuator 20. In other words, an internal pressure of the actuator 20 in the first state can be the same or generally similar to the internal pressure of the actuator 20 in the second state. For example, the second elastic diaphragm 64 can collapse inwardly and the first elastic diaphragm 62 can expand outwardly as shown. The inwardly collapsing second diaphragm 64 can avoid the generation of a vacuum in the second chamber 76, thereby lowering the pressure differential used to create the same force on the movable element 28 of the valve 2. Therefore, the first chamber 74 and the second chamber 76 can comprise expandable or deformable chambers. The first elastic diaphragm 62 and the second elastic diaphragm 64 can comprise any suitable material. In some embodiments, the first elastic diaphragm 62 and/or the second elastic diaphragm 64 can comprise silicon rubber or high consistency rubber. In some embodiments, the first elastic diaphragm 62 and the second elastic diaphragm 64 can comprise the same material or different materials.

In some embodiments, the first electrode 68 and the second electrode 70 can comprise micro-pores (not illustrated). The micro-pores can allow the solution to flow across the first electrode 68 and the second electrode 70 (between the first chamber 74 and the second chamber 76). The micro-pores are large enough for the solution to pass through but small enough for providing a sufficient magnetic field during operation of the valve 2. In some embodiments, a length l1 of a side of the micro-pore of the first electrode 68 and the second electrode 70 can be less than about 10 μm. In some embodiments, there can be a gap (not illustrated) between the first electrode 68 and the porous membrane 72. Likewise, there can be a gap (not illustrated) between the first electrode 68 and the porous membrane 72. In some embodiments, the gap can be provided by the spacer 66. In some embodiments, the gap can be in a range from 20 μm to 30 μm. The gap can be about 25 μm in some embodiments. In some applications, the gap can facilitate fluid flow between the first chamber 74 and the second chamber 76. For example, absent the gap, it may be less efficient for the solution to go through the porous membrane 72, the first electrode 68, and/or the second electrode 70 than with the gap. The gap can be sufficiently narrow such that the voltage applied to the first electrode 68 and the second electrode 70 can create a desired electroosmosis reaction.

The porous membrane 72 can comprise any suitable material. In some embodiments, the porous membrane 72 can comprise silicon, glass aluminum, or polymer. The porous membrane 72 can comprise pores. In some embodiments, a size of the pore of the porous membrane 72 can be in a range from, for example, 100 nanometer (nm) to 200 nm, in a range from, for example, 100 nm to 150 nm, or in a range from, for example, 150 nm to 200 nm. In some embodiments, the pores of the porous membrane 72 have a porosity in a range from, for example, 40% to 60%, in a range from, for example, 50% to 60%, or in a range from, for example, 40% to 50%.

The actuator 20 has a height h, lengths l1, l2 in a direction perpendicular to the height. In the illustrated embodiment, the length l1, l2 of the actuator 20 are the same. However, in some other embodiments, the lengths l1, l2 can be different. In some embodiments, the height h of the actuator 20 can be smaller than about 3 mm. Is some embodiments, the height h of the actuator 20 can be in a range of, for example, 1 mm to 3 mm, in a range of, for example, 2 mm to 3 mm, or in a range of, for example, 2.5 mm to 3 mm. In some embodiments, an area formed by the length l1, l2 can be less than about 100 mm². In some embodiments, the length l1, l2 of the actuator 20 can be about 10 mm. Is some embodiments, the length l1, l2 of the actuator 20 can be in a range of, for example, 5 mm to 15 mm, in a range of, for example, 5 mm to 10 mm, or in a range of, for example, 8 mm to 12 mm. In some applications, having the dimension of the actuator 20 relatively small can be beneficial. In such actuator 20 with small dimension can require relatively low power to operate and provide relatively fast response time for an electroosmosis reaction.

An example operation of the actuator 20 will be described with reference to FIGS. 3A-5C. In the first state illustrated in FIGS. 3A, 4A and 5A, the solution in the actuator 20 can be in an equilibrium state. For example, in some embodiments, in the first state, no external power (voltage) may be applied to the first electrode 68 and the second electrode 70. In the first state, no electroosmotic flow is created from the second chamber 76 to the first chamber 74 (or vice versa). In the first state, the first elastic diaphragm 62 and the second elastic diaphragm 64 can be relaxed. Therefore, no force is applied to the movable element 28 by the actuator 20 in the first state.

In the second state illustrated in FIGS. 3B, 4B, 5B and 5C, electrical power (voltage) is applied to the first electrode 68 and the second electrode 70. The second state comprises a state in which an external force applied by the actuator 20 is sufficient to move the movable element 28 to at least partially open the gate 24 of the gate structure 22. In the second state, a pressure difference between the first chamber 74 and the second chamber 76 created by the applied voltage can create an electroosmotic flow of the solution from the second chamber 76, through the porous membrane 72, and into the first chamber 74. The electroosmotic flow in the second state is shown with arrows in FIG. 4B. The electroosmotic flow can be controlled by controlling the applied voltage. In some embodiments, a coin cell battery can provide the voltage. In some embodiments, the actuator 20 can operate with applied voltage of less than about 5V.

Referring to FIG. 4B, the first elastic diaphragm 62 can protrude from the housing 60 in response to the electroosmotic flow of the solution. The protruded portion of the first elastic diaphragm 62 has a displacement d and a volume v. The displacement d and the volume v can be interrelated. The displacement d and the volume v can be controlled by changing the voltage applied to the first electrode 68 and the second electrode 70. For example, when a lower voltage is applied, the displacement d and the volume v can be smaller than when a higher voltage is applied. By controlling the applied voltage, the displacement d and the volume v can be controlled. In turn, a size of the exposed portion of the opening 25 of the gate 22 of the valve 2 (see FIG. 3B) can be controlled, and in turn, the flow rate of fluid through the exposed portion of opening 25. As described above, the opening 25 can be exposed when at least a portion of the opening 25 and the hole 27 align with each other. In some embodiments, a maximum value of the volume v can be in a range of, for example, 25 μL to 3 mL, in a range of, for example, 25 μL to 2 mL, in a range of, for example, 25 μL to 1 mL, in a range of, for example, 25 μL to 100 μL, in a range of, for example, 100 μL to 3 mL, in a range of, for example, 25 μL to 75 μL, or in a range of, for example, 50 μL to 75 μL.

Figures 6A, 6B:
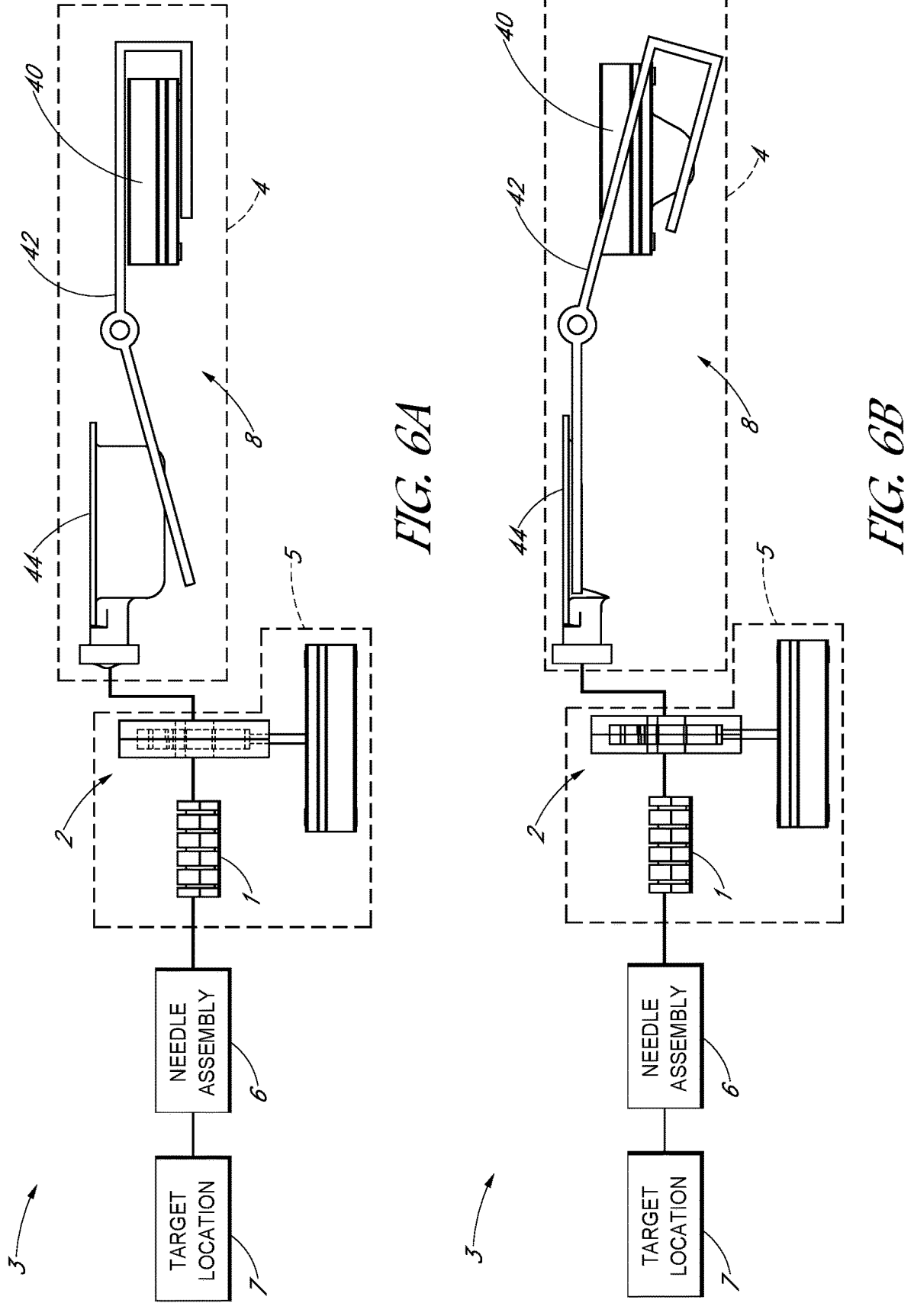
FIG. 6A illustrates a schematic system diagram of a substance delivery system in a first state according to one embodiment.
FIG. 6B illustrates a schematic system diagram of the substance delivery system 3 illustrated in FIG. 6A in a second state.

FIG. 6A illustrates a schematic system diagram of a substance delivery system 3 that includes a substance delivery device 4, a flow control system 5, and needle assembly 6, in a first state according to one embodiment. FIG. 6B illustrates a schematic system diagram of the substance delivery system 3 illustrated in FIG. 6A in a second state. The flow control system 5 can comprise the flow meter 1 and the valve 2 illustrated in FIGS. 1-3B. The substance delivery system 3 can deliver a substance from the substance delivery system 4 through the flow control system 5 and the needle assembly 6 to a target location 7. The target location 7 can be, for example, inside of a patient's body (for example, inside the vascular system of the patient), or an external device (for example, analysis equipment configured to analyze or test blood, drugs, or other fluids).

The substance delivery system 4 can comprise a substance delivery device 8 that include a pump 40 and lever 42, and a container 44. In some embodiments, the pump 40 can comprise an EO pump. The container 44 (e.g., a drug pod) can be configured to receive and hold a fluid substance (e.g., a drug). The substance delivery system 4 can also include a packaging structure (not illustrated) which can package the pump 40, lever 42, and the container 14. Additional details of substance delivery systems may be found at least in U.S. application Ser. No. 16/851,798, the entire contents of which are incorporated by reference herein in their entirety and for all purposes.

The flow control system 5 can be positioned downstream of the substance delivery system 4. For example, the flow control system 5 can be positioned between the substance delivery system 4 and the target location 7 (e.g., a patient's body). In some embodiments, the flow control system 5 can control an operation of the substance delivery system 4. In FIGS. 6A and 6B, the flow meter 1 is positioned downstream of the valve 2. However, in some embodiments, the flow meter 1 can be positioned upstream of the valve 2.

Figure 7:
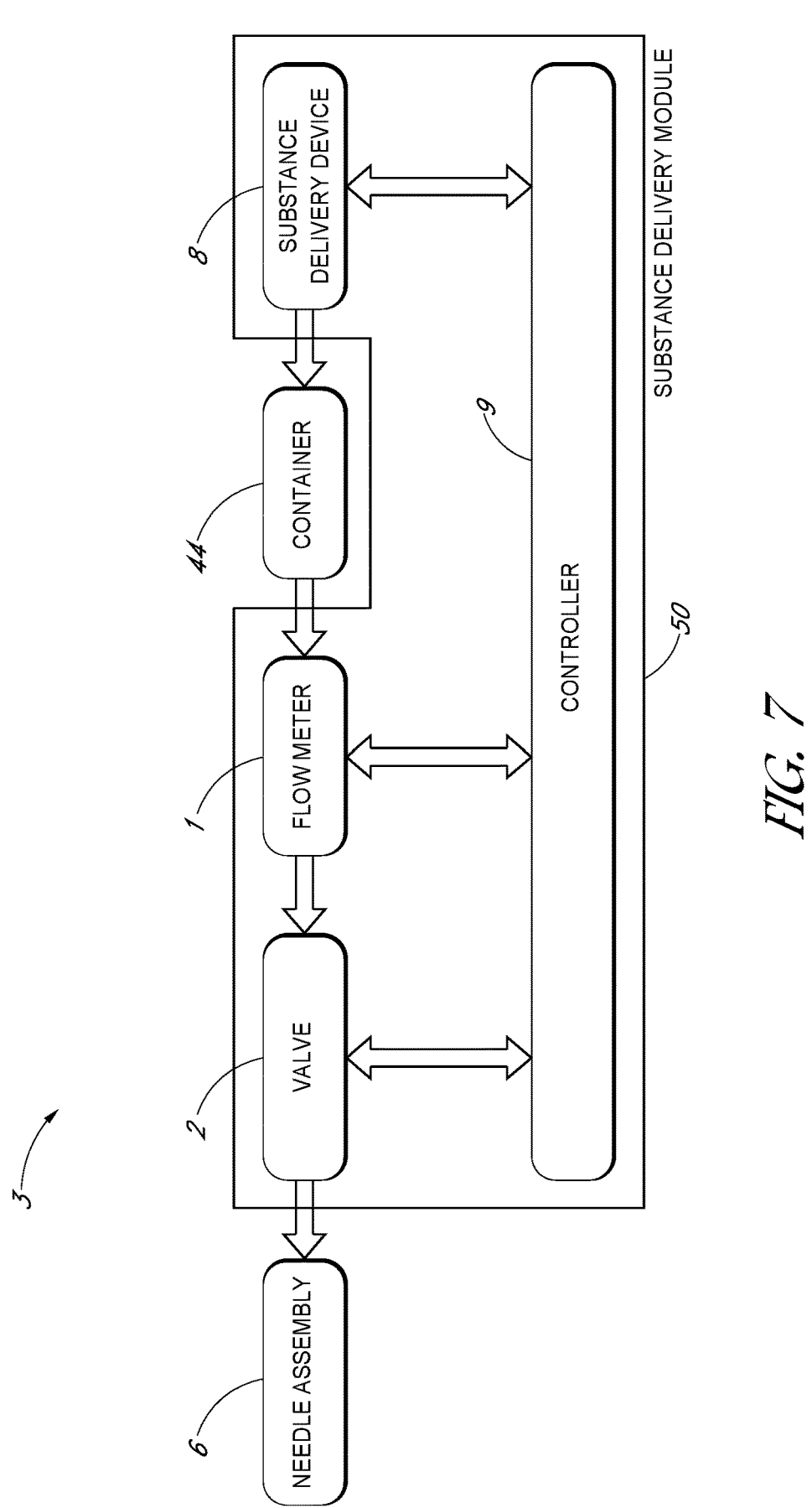
FIG. 7 is a block diagram of a substance delivery system according to one embodiment.

FIG. 7 is a block diagram of a substance delivery system 3 according to one embodiment. The substance delivery system 3 can include a substance delivery device 8, 8, a container 44, a flow meter 1, a valve 2, a needle assembly 6, and a controller 9. In some embodiments, the substance delivery device 8, the flow meter 1, the valve 2, and the controller 9 can define a substance delivery module 50. In some embodiments, the valve 2 may be positioned between the substance delivery device 8 and the flow meter 1.

The flow meter 1 can monitor a flow rate and/or a flow amount of the substance flowing through the flow meter 1 from the container 44. The valve 2 can prevent or mitigate a backflow of the substance. In some embodiments, the valve 2 can control the substance flow. The controller 9 can control operation of the substance delivery module 50. The controller 9 can include processing electronics that are programmed to control operations of the substance delivery system 3. The controller 9 can include one or more processors, one or more memory devices, etc. For example, the substance delivery device 8, the flow meter 1, and/or the valve 2 can connect to the controller 9, and can be controlled by the controller 9. In some embodiments, the substance delivery device 8, the flow meter 1, and the valve 2 can be connected to the controller 9 through a wired connection, or wirelessly (e.g., electromagnetically). In some embodiments, the controller 9 can comprise or be connected to a user interface (including, e.g., buttons, displays, etc.) that can allow a user to control the substance delivery module 50, or to monitor the activities of the substance delivery module 50. In some embodiments, the controller 9 can be connected to other sensors, such as an accelerometer, thermometer, etc. In some embodiments, the controller 9 can be connected to a vital sign monitoring device. In some embodiments, the controller 9 can be programmed to deliver a programmed amount of a substance (e.g., a drug) to a target location over time. For example, the controller 9 can be programmed such that after a time period T(x), a voltage V(x) is applied across the first electrode 68 and the second electrode 70. In response to the voltage V(x) applied, the elastic displacement d and the volume v can be increased and/or decreased, depending on the desired dosage to be delivered to the patient at a particular time.

In some applications, the flow meter 1 can monitor a flow of a fluid substance to measure a delivered volume of the substance, a flow rate, and/or a flow direction (e.g., forward flow or backflow). The measured data can be compared against a predetermined or prescribed dosage of the substance. The measured data can be used to regulate the voltage on the actuator 20 of the valve 2 and/or the pump 40 of the substance delivery device 8. The measured data can be used to operate, for example, the valve 2 (e.g., a shutoff valve or check valve) and/or the substance delivery device 8.

In some applications, the controller 9 can be programmed to send a start signal to the substance delivery device 8 to activate the substance delivery device 8 at a predetermined time, on command from the user or clinician, or based on other criteria. In response, the substance delivery device 8 can drive a substance from the container 44 through a flow path by way of the flow meter 1, the valve 2, and the needle assembly 6 to a target location. The controller 9 can transmit a valve open signal to open the valve 2 so as to allow the substance to flow through the flow path. The controller can transmit electrical energy (e.g., provide current) to the flow meter 1 to heat the heating elements (see FIGS. 1 and 2). The controller can receive a signal from the sensing elements (see FIGS. 1 and 2) of the flow meter 1. The controller 9 can determine a flow rate based at least in part on the electrical energy transmitted to the flow meter 1, the signal received from the flow meter 1, and known properties of the substance. In some embodiments, the controller 9 can determine a volume of the substance delivered through the flow meter 1 based on the flow rate. After a particular volume has been delivered through the flow meter 1, the controller 9 can transmit a valve close signal to the valve 2 to close the valve 2 and a stop signal to the substance delivery device 8 to stop driving the substance. In some embodiments, the controller 9 can be programmed to open the valve 2 at a particular time, in response to a command from a user, or when certain occurrence takes place (e.g., when a blood sugar level rises over a particular level). In some embodiments, the controller 9 can control the operation of the substance delivery device 8 to control the flow rate of the substance. In some embodiments, the controller 9 may transmit flow data (e.g., the flow rate and the flow amount) to an external device, such as a smart phone (not illustrated).

The needle assembly 6 can comprise a conduit (e.g., a tube) and a needle that is coupled to the conduit. In some applications, the needle can be inserted into a patient's body through the skin such that the fluid substance (e.g., drug) delivered from the container by the substance delivery module 50 is conveyed to an interior of the patient (e.g., the patient's vascular system) through the needle assembly 6.

Although disclosed in the context of certain embodiments and examples, it will be understood by those skilled in the art that the present invention extends beyond the specifically disclosed embodiments to other alternative embodiments and/or uses and obvious modifications and equivalents thereof. In addition, while several variations have been shown and described in detail, other modifications, which are within the scope of this disclosure, will be readily apparent to those of skill in the art based upon this disclosure. It is also contemplated that various combinations or sub-combinations of the specific features and aspects of the embodiments may be made and still fall within the scope of the present disclosure. It should be understood that various features and aspects of the disclosed embodiments can be combined with, or substituted for, one another in order to form varying modes of the disclosed invention. Thus, it is intended that the scope of the present invention herein disclosed should not be limited by the particular disclosed embodiments described above, but should be determined only by a fair reading of the aspects that follow.

What is claimed is:

1. A fluid delivery system to deliver a biocompatible fluid comprising:
   a valve positioned at a first location of a flow path of a fluid substance, the valve including,
   an actuator comprising a deformable chamber, and
   a gate structure, the gate structure comprising a gate in the flow path of the fluid substance and having an opening, a housing comprising a hole, and a movable element,
   wherein when the actuator is activated, the actuator applies force to the movable element to open the gate so that the opening of the gate and the hole of the housing are at least partially aligned along a same axis,
   wherein the actuator applies the force to the movable element in response to deformation of the deformable chamber so as to allow the fluid substance to flow in the flow path;
   wherein the opening of the gate and the hole of the housing are not aligned when the gate is closed; and
   wherein a position of the opening relative to the hole is configured to change when the actuator is activated.

2. The fluid delivery system of claim 1, wherein the actuator comprises an electroosmotic (EO) pump.

3. The fluid delivery system of claim 2, wherein the EO pump comprises a second deformable chamber, a porous electrode positioned between the deformable chamber and the second deformable chamber, and a porous membrane positioned between the deformable chamber and the second deformable chamber, the deformable chamber and the second deformable chamber being in fluid communication.

4. The fluid delivery system of claim 1, further comprising a flow meter positioned at a second location of the flow path of the fluid substance, wherein the flow meter comprises a molded non-conductive housing, a heating element at least partially embedded in the molded non-conductive housing, and a sensing element at least partially embedded in the molded non-conductive housing.

5. The fluid delivery system of claim 4, further comprising a pump configured to drive the fluid substance along the flow path through the valve and the flow meter.

6. The fluid delivery system of claim 1, further comprising a controller in electrical communication with the valve, the controller configured to control operation of the fluid delivery system.

7. A fluid delivery system to deliver a biocompatible fluid comprising:

a flow meter positioned in a fluid flow path;

a valve positioned in the fluid flow path, the valve including an actuator comprising, a first elastic diaphragm and a second elastic diaphragm;

a first deformable chamber and a second deformable chamber positioned between the first elastic diaphragm and the second elastic diaphragm, wherein, when the actuator is activated, the first deformable chamber and the second deformable chamber are configured to actuate a gate to open the fluid flow path to allow a fluid substance to flow through the fluid flow path;

a porous membrane positioned between the first deformable chamber and the second deformable chamber; and a pump configured to drive the fluid substance along the fluid flow path through the valve and the flow meter;

wherein the first deformable chamber is configured to expand in response to an electroosmotic flow of a solution through the actuator;

wherein the fluid flow path is open when the first deformable chamber is in an expanded position.

8. The fluid delivery system of claim 7, wherein the valve comprises an electroosmotic (EO) pump.

9. The fluid delivery system of claim 7, wherein the pump comprises an electroosmotic (EO) pump.

10. The fluid delivery system of claim 7, wherein the flow meter further comprises a molded non-conductive housing, a heating element at least partially embedded in the molded non-conductive housing, and a sensing element at least partially embedded in the molded non-conductive housing.

11. The fluid delivery system of claim 7, further comprising a controller in electrical communication with the flow meter, the valve, and the pump, the controller configured to control operation of the fluid delivery system.

12. A fluid delivery system to deliver a biocompatible fluid comprising:

a flow meter positioned at a first location of a flow path of a fluid substance, the flow meter comprising a molded non-conductive housing, an opening extending an entire length of the molded non-conductive housing, a plurality of heating elements at least partially embedded in the molded non-conductive housing and exposed to the flow path, and a plurality of sensing elements at least partially embedded in the molded non-conductive housing and exposed to the flow path, wherein the plurality of heating elements are configured to transfer first thermal energy to the fluid substance in the flow path, and the plurality of sensing elements are configured to transduce second thermal energy from the flow path to an electrical signal, wherein the plurality of heating elements and the plurality of sensing elements are spaced apart from each other along a length of the molded non-conductive housing; and wherein each of the plurality of heating elements and the plurality of sensing elements comprises a curved portion, a first foot extending radially outward from the curved portion and comprising a first terminal, a second foot extending radially outward from the curved portion and comprising a second terminal, and a gap between the first foot and the second foot;

wherein each of the first terminals and second terminals is at least partially exposed to an exterior of the molded non-conductive housing.

13. The fluid delivery system of claim 12, wherein the plurality of heating elements and the plurality of sensing elements are arranged to contact the fluid substance during operation of the fluid delivery system.

14. The fluid delivery system of claim 12, wherein the plurality of heating elements comprises a conductive plastic, and the plurality of heating elements is disposed at least partially around a portion of the flow path.

15. The fluid delivery system of claim 12, wherein the opening comprises a diameter in a range from 0.5 mm to 1 mm.

16. The fluid delivery system of claim 12, wherein a volume of the flow path in the flow meter is between 0.1 $mm^3$ to 16 $mm^3$.

17. The fluid delivery system of claim 12, further comprising a valve positioned at a second location of the flow path of the fluid substance, the valve configured to control a flow of the fluid substance along the flow path, wherein the valve comprises an actuator including a deformable chamber.

18. The fluid delivery system of claim 17, wherein the valve comprises a gate positioned in the flow path, the gate configured to open in response to deformation of the deformable chamber thereby allowing the fluid substance to flow in the flow path.

19. The fluid delivery system of claim 17, wherein the actuator comprises an electroosmotic (EO) pump.

20. The fluid delivery system of claim 12, further comprising a controller in electrical communication with the flow meter, the controller configured to control operation of the fluid delivery system, wherein the controller is configured to transmit current to the plurality of heating elements, to receive the electrical signal from the plurality of sensing elements, and to determine at least one of a temperature and a flow rate based at least in part on the electrical signal.

21. The fluid delivery system of claim 12, wherein each of the first terminals comprises an anode terminal and each of the second terminals comprises a cathode terminal.

22. The fluid delivery system of claim 12, wherein each of the first terminals and each of the second terminals comprise a dual in-line package structure configured to be mounted to a printed circuit board.

\* \* \* \* \*